United States Patent [19]

Sih

[11] 4,284,795

[45] Aug. 18, 1981

[54] 19,20-DIDEHYDRO-PG$_2$ COMPOUNDS

[75] Inventor: John C. Sih, Kalamazoo, Mich.

[73] Assignee: The Upjohn Company, Kalamazoo, Mich.

[21] Appl. No.: 85,620

[22] Filed: Oct. 17, 1979

Related U.S. Application Data

[62] Division of Ser. No. 26,066, Apr. 2, 1979, Pat. No. 4,243,611.

[51] Int. Cl.$^3$ .......................................... C07C 177/00
[52] U.S. Cl. .................. 560/121; 562/503; 260/404; 260/404.5; 260/408; 260/410; 260/410.5; 260/410.9 R; 260/413
[58] Field of Search ................ 560/121; 562/503; 260/404, 404.5, 408, 410, 410.5, 410.9 R, 413

[56] References Cited

U.S. PATENT DOCUMENTS

| | | | |
|---|---|---|---|
| 3,919,285 | 11/1975 | Axen | 560/121 |
| 4,064,351 | 12/1977 | Sakai et al. | 560/121 |

FOREIGN PATENT DOCUMENTS 2635985  2/1978  Fed. Rep. of Germany ........... 560/121

*Primary Examiner*—Robert Gerstl
*Attorney, Agent, or Firm*—Lawrence T. Welch; Robert A. Armitage

[57] ABSTRACT

The present invention provides novel 19,20-didehydro-PG$_2$ compounds, methods for their preparation and pharmacological use for the induction of prostaglandin-like effect.

3 Claims, No Drawings

19,20-DIDEHYDRO-PG₂ COMPOUNDS

CROSS REFERENCE TO RELATED APPLICATIONS

The present application is a division of Ser. No. 026,066, filed Apr. 2, 1979, now U.S. Pat. No. 4,243,611.

BACKGROUND OF THE INVENTION

The present invention relates to novel prostaglandin analogs. Particularly, these compounds are analogs of the prostaglandins wherein the C-20-C-19 position is unsaturated, i.e., 19,20-didehydro-PG compounds. Most particularly, the present invention relates to novel 19,20-didehydro-PG₂ compounds, a disclosure of the preparation and use of which is incorporated here by reference from U.S. Pat. No. 4,228,104.

PRIOR ART

Prostaglandin analogs exhibiting unsaturation in the C-17, C-18, or C-20 position are known in the art. See, for example, U.S. Pat. No. 3,919,285 German Offenlegungsschrift No. 2,635,985 (and its corresponding Derwent Farmdoc CPI No. 10302A), and U.S. Pat. No. 4,064,351 for examples of such compounds. See also the references cited in U.S. Ser. No. 026,066.

SUMMARY OF THE INVENTION

The present invention particularly provides:
A compound of the formula

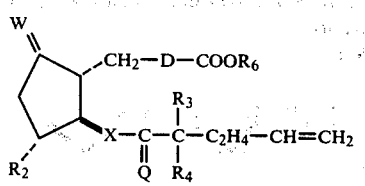

wherein D is
  (1) cis—CH=CH—CH₂—(CH₂)$_g$—CH₂—,
  (2) cis—CH=CH—CH₂—(CH₂)$_g$—CF₂—,
  (3) cis—CH₂—CH=CH—CH₂—CH₂—,
  (4) trans—(CH₂)₃—CH=CH—,
wherein g is zero, one, 2, or 3;
wherein Q is

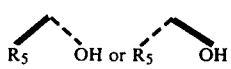

wherein R₅ is hydrogen or methyl,
wherein R₆ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl groups of one to 3 carbon atoms, inclusive;

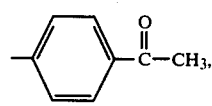

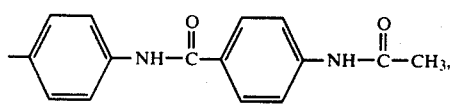

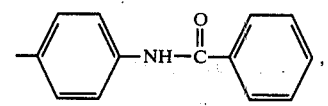

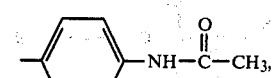

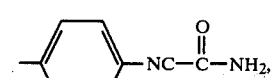

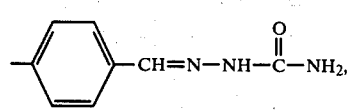

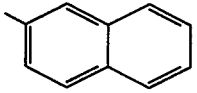

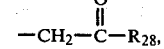

wherein R₂₈ is phenyl, p-bromophenyl, p-biphenylyl, p-nitrophenyl, p-benzamidophenyl, or 2-naphthyl, or
(o) a pharmaceutically acceptable cation; wherein e R₇ and R₈ are hydrogen, alkyl of one to 12 carbon atoms, inclusive, benzyl, or phenyl, being the same or different; and wherein R₂₉ is hydrogen, alkyl of one to 12 carbon atoms, inclusive, aralkyl of 7 to 12 carbon atoms, inclusive, phenyl, phenyl ates Ser. substituted with one, 2, or 3 chloro or alkyl groups of one to 3 carbon atoms, inclusive, or phenyl substituted with hydroxycarbonyl or alkoxycarbonyl of one to 4 carbon atoms, inclusive;
wherein R₂ is hydrogen, hydroxyl, or hydroxymethyl;
wherein R₃ and R₄ are hydrogen, methyl, or fluoro, mabeing the same or different, with the proviso that one of R₃ and R₄ is fluoro only when the other is hydrogen or fluoro;
wherein W is

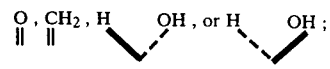

and wherein X is cis— or trans—CH=CH— or —C≡C—.

Specific embodiments of the present invention include
19,20-didehydro-PGF₂α, methyl ester and
15(R)-19,20-didehydro-PGF₂α, methyl ester.

The compounds of the present invention are particularly useful for inducing prostaglandin-like biological effects, as is described in U.S. Ser. No. 026,066. Use of compounds in accordance with the present invention include, therefore, anti-asthmatic indication.

I claim:
1. A compound of the formula

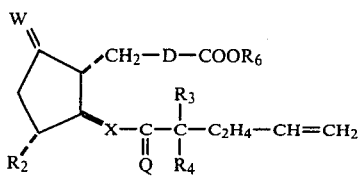

wherein D is
(1) cis—CH=CH—CH$_2$—(CH$_2$)$_g$—CH$_2$—,
(2) cis—CH=CH—CH$_2$—(CH$_2$)$_g$—CF$_2$,
(3) cis—CH$_2$—CH=CH—CH$_2$—CH$_2$—,
(4) trans—(CH$_2$)$_3$—CH=CH—,
wherein g is zero, one, 2, or 3;
wherein Q is

wherein R$_5$ is hydrogen or methyl,
wherein R$_6$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl groups of one to 3 carbon atoms, inclusive;

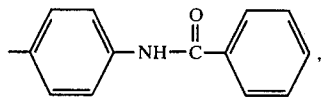 (g)

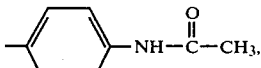 (h)

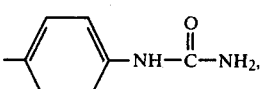 (i)

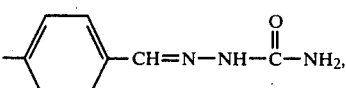 (j)

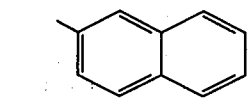 (k)

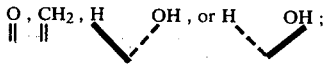 (l)

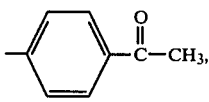 (m)

—CH$_2$—C(=O)—R$_{28}$, (n)

wherein R$_{28}$ is phenyl, p-bromophenyl, p-biphenylyl, p-nitrophenyl, p-benzamidophenyl, or 2-naphthyl, or
(o) a pharmacologically acceptable cation;
wherein R$_2$ is hydrogen, hydroxyl, or hydroxymethyl;
wherein R$_3$ and R$_4$ are hydrogen, methyl, or fluoro, being the same or different, with the proviso that one of R$_3$ and R$_4$ is fluoro only when the other is hydrogen or fluoro;
wherein W is $$\overset{O}{\|}, \overset{CH_2}{\|}, \overset{H}{\diagdown}\overset{OH}{\diagup}, \text{ or } \overset{H}{\diagdown}\overset{OH}{\diagup};$$

and wherein X is cis— or trans—CH=CH— or —C≡C—.

2. 19,20-Didehydro-PGF$_{2\alpha}$, methyl ester, a compound according to claim 1.

3. 15(R)-19,20-Didehydro-PGF$_{2\alpha}$, methyl ester, a compound according to claim 1.

* * * * *

UNITED STATES PATENT AND TRADEMARK OFFICE
CERTIFICATE OF CORRECTION

PATENT NO. : 4,284,795

DATED : 18 August 1981

INVENTOR(S) : John C. Sih

It is certified that error appears in the above—identified patent and that said Letters Patent is hereby corrected as shown below:

Column 2, line 36, "phenyl ates Ser. substituted" should read -- phenyl substituted --.

Column 2, line 44, "mabeing the same" should read -- being the same --.

Signed and Sealed this

Twenty-second Day of December 1981

[SEAL]

Attest:

GERALD J. MOSSINGHOFF

Attesting Officer     Commissioner of Patents and Trademarks